(12) United States Patent
Xu et al.

(10) Patent No.: US 12,310,866 B2
(45) Date of Patent: *May 27, 2025

(54) METHODS AND DEVICES FOR PERFORMING ELECTROSURGERY

(71) Applicant: Boston Scientific Scimed, Inc., Maple Grove, MN (US)

(72) Inventors: Mingxiang Xu, Wayland, MA (US); Samuel Raybin, Marlborough, MA (US); Paul Smith, Smithfield, RI (US); Kevin James McElwee, Franklin, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 214 days.

This patent is subject to a terminal disclaimer.

(21) Appl. No.: 18/083,616

(22) Filed: Dec. 19, 2022

(65) Prior Publication Data

US 2023/0123655 A1  Apr. 20, 2023

Related U.S. Application Data

(63) Continuation of application No. 16/366,131, filed on Mar. 27, 2019, now Pat. No. 11,553,959.

(Continued)

(51) Int. Cl.
*A61B 18/14* (2006.01)
*A61B 1/018* (2006.01)
(Continued)

(52) U.S. Cl.
CPC .............. *A61F 2/82* (2013.01); *A61B 1/018* (2013.01); *A61B 1/04* (2013.01); *A61B 18/1206* (2013.01);
(Continued)

(58) Field of Classification Search
CPC .. A61F 2/82; A61B 1/018; A61B 1/04; A61B 18/1206; A61B 18/1492; A61B 18/16; A61B 2017/00004; A61B 2018/00273; A61B 2018/00577; A61B 2018/00589; A61B 2018/00601; A61B 2018/00982; A61B 2018/1475
See application file for complete search history.

(56) References Cited

U.S. PATENT DOCUMENTS 5,348,554 A * 9/1994 Imran ................ A61B 18/1492
606/41
6,007,512 A 12/1999 Hooven
(Continued)

*Primary Examiner* — Michael F Peffley
*Assistant Examiner* — Bo Ouyang
(74) *Attorney, Agent, or Firm* — Bookoff McAndrews PLLC

(57) ABSTRACT

According to one aspect, a medical system may include an instrument including an end effector for acting as a monopolar electrode. The end effector may be configured to be positioned in a body of a subject and emit radiofrequency energy towards a target area in the body. The medical system may further include a return electrode. The return electrode may be deliverable within the body proximate the target area and separately from the instrument and the monopolar electrode. The return electrode may be configured to contact tissue in the body proximate the target area and receive radiofrequency energy emitted from the end effector.

20 Claims, 8 Drawing Sheets

Related U.S. Application Data

(60) Provisional application No. 62/649,696, filed on Mar. 29, 2018.

(51) Int. Cl.
  *A61B 1/04* (2006.01)
  *A61B 18/12* (2006.01)
  *A61B 18/16* (2006.01)
  *A61F 2/82* (2013.01)
  *A61B 17/00* (2006.01)
  *A61B 18/00* (2006.01)

(52) U.S. Cl.
  CPC .......... *A61B 18/1492* (2013.01); *A61B 18/16* (2013.01); *A61B 2017/00004* (2013.01); *A61B 2018/00273* (2013.01); *A61B 2018/00577* (2013.01); *A61B 2018/00589* (2013.01); *A61B 2018/00601* (2013.01); *A61B 2018/00982* (2013.01); *A61B 2018/1475* (2013.01)

(56) References Cited

U.S. PATENT DOCUMENTS

| | | | |
|---|---|---|---|
| 7,297,143 B2 * | 11/2007 | Woloszko | A61B 18/1492 606/41 |
| 2003/0065364 A1 * | 4/2003 | Wellman | A61B 18/1482 607/5 |
| 2003/0158545 A1 | 8/2003 | Hovda et al. | |
| 2006/0271089 A1 * | 11/2006 | Alejandro | A61M 25/0069 606/192 |
| 2007/0244478 A1 | 10/2007 | Bahney | |
| 2009/0076498 A1 | 3/2009 | Saadat et al. | |
| 2016/0303381 A1 * | 10/2016 | Pierce | A61B 18/1815 |
| 2018/0228538 A1 * | 8/2018 | Roeder | A61B 18/1492 |

\* cited by examiner

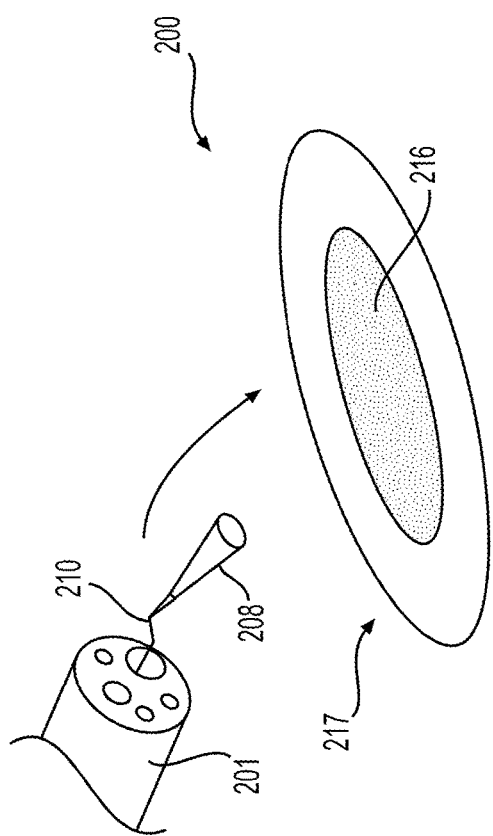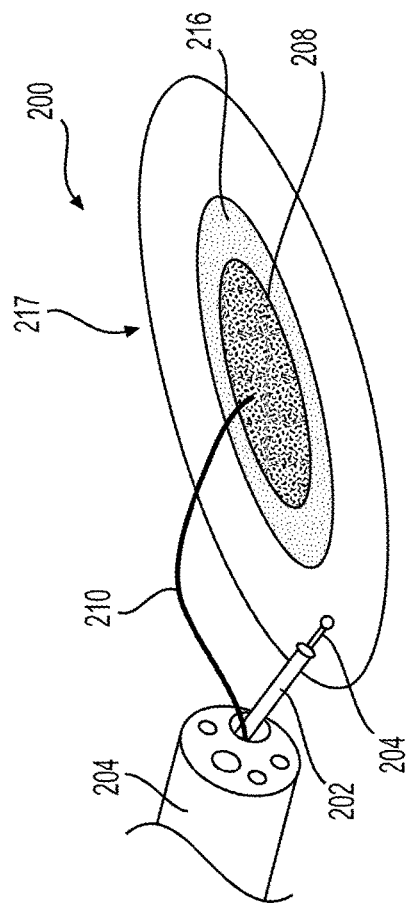

METHODS AND DEVICES FOR PERFORMING ELECTROSURGERY

CROSS-REFERENCE TO RELATED APPLICATIONS

This application is a continuation of U.S. patent application Ser. No. 16/366,131, filed on Mar. 27, 2019, which claims the benefit of priority from U.S. Provisional Application No. 62/649,696, filed Mar. 29, 2018, which are each incorporated by reference herein in their entirety.

TECHNICAL FIELD

The present disclosure relates generally to surgical instruments and related systems and methods. More particularly, the present disclosure relates to electrosurgery devices, systems, and methods for providing treatment of tissue.

BACKGROUND

Medical devices are often used to extract undesired and/or foreign material from the body. These medical devices use various extraction methods, such as dissection, coagulation, fulguration, ablation, etc., of undesired body matter. An example of a type of procedure that uses such methods is electrosurgery. Electrosurgery involves the application of energy to biological tissue to cut, coagulate, desiccate, or fulgurate tissue. Electrosurgery uses various types of high-frequency electrical energy to directly heat the tissue.

Generally, electrosurgery is performed using a radio frequency electrosurgical generator and a hand piece including one or two electrodes. A monopolar instrument comprises only one active electrode while a bipolar instrument includes two active electrodes at the surgical site. The monopolar instrument requires the application of another instrument called a dispersive or return electrode elsewhere on or otherwise coupled to the patient's body to defocus or disperse the radio frequency current and returning the energy to the electrosurgical generator to prevent injury to the underlying tissue. However, often injury to the patient can occur from the energy traveling a large distance from the active electrode through the body to the return electrode. Also, doctors must be careful to avoid complications such as direct coupling, insulation failure, and capacitive coupling, among other potential complications that may result in patient injury.

A bipolar electrosurgical instrument typically includes forceps or other end effectors with the two tines of the forceps performing the active and return electrode functions, with only the tissue grasped by the forceps included in the electrical circuit. Bipolar instruments require less voltage than monopolar instruments, and since the active and return electrodes are at the site of surgery, the risk of accidental injury to the patient is less compared to monopolar devices. Bipolar instruments perform well when sealing vessels, however they include lateral thermal spread that will continue until the device activation is ceased. Bipolar electrosurgical instruments are limited in their application and provide less precise cutting compared to monopolar instruments. There is a need for a hybrid between monopolar and bipolar electrosurgical instruments that may utilize voltages similar to bipolar instruments and yet have similar cutting power to monopolar instruments.

Conventional electrosurgical devices often have large profiles and are not configured to be inserted into difficult to reach areas of the body or for use with endoscopic devices. There is a need for an electrosurgical device with a small cutting electrode that mitigates thermal perforation while maintaining a high level of cutting performance. Furthermore, there is a need for an electrosurgical device optimized for use in endoscopic procedures.

SUMMARY

Embodiments of the present disclosure relate to, among other things, surgical devices and methods of using the same for providing electric energy treatment of body tissue. Each of the embodiments disclosed herein may include one or more of the features described in connection with any of the other disclosed embodiments.

According to one aspect, a medical system may include an instrument. The instrument may include an end effector for acting as a monopolar electrode. The end effector may be configured to be positioned in a body of a subject and emit radiofrequency energy towards a target area in the body. The medical system may further include a return electrode. The return electrode may be uncoupled from the instrument proximate the target area and/or along its extent extending toward a proximal end of the instrument, and deliverable within the body proximate the target area and separately from the instrument and the monopolar electrode. The return electrode may be configured to contact tissue in the body proximate the target area and receive radiofrequency energy emitted from the end effector.

In other aspects of the present disclosure, the medical system may include one or more of the features below. The medical system may include a shaft having a distal end and a plurality of lumens, the instrument may be deliverable in a first lumen of the plurality of lumens, and the return electrode may be deliverable in a second lumen of the plurality of lumens or alongside an external surface of the shaft. The return electrode may be planar and flexible, and may include structure to couple the return electrode to tissue. The return electrode may have an expanded state and a retracted state. The return electrode may be configured to transition from a retracted state to an expanded state when exiting a lumen of a delivery device. The return electrode may have a toroid shaped. Also, the return electrode may include at least one clip. The medical system may further include an energy generator for delivering radiofrequency energy to the monopolar electrode and receiving radiofrequency energy from the return electrode. The return electrode may be at least one of absorbable and degradable. In some aspects, the return electrode may include a stent.

In other aspects, a method for treating tissue in a target area within a patient's body may include delivering a return electrode proximate to the target area. The method may also include, separate from delivering the return electrode, delivering an instrument having an end effector proximate to the target area. The end effector may act as an electrode. Also, the method may include emitting radiofrequency energy from the end effector and toward the target area. The method may further include receiving the radiofrequency energy with the return electrode.

In other aspects of the present disclosure, the method for treating tissue may further include one or more of the features below. The method may also include positioning a distal end of a shaft of a medical device adjacent the target area. The target area may be within the body of a patient. Also, the method may include visualizing a surface of the target area using an imaging sensor. The method may further include cutting, dissecting, ablating, coagulating, or fulgurating tissue within the body of the patient via the end effector. In addition, the method may include expanding the return electrode from a retracted state to an expanded state. The return electrode may include at least two clips, and the method may include creating tension in at least one surface of the target area via the at least two clips of the return electrode. The method may also include surrounding a lesion with the return electrode. The return electrode may include a stent, and the method may include expanding the stent within a body lumen of the patient. Also, the method may include delivering a shaft proximate to the target area and the instrument may be delivered to the target area through a lumen of the shaft, and the instrument may be delivered to the target area outside of the shaft.

In other aspects of the present disclosure, a method for performing a therapy within a body of a patient may include positioning a distal end of a shaft of a medical device adjacent a target area. The target area may be within the body of a patient, and the medical device may include at least one working lumen. The method may also include positioning a return electrode at or proximate to the target area. In addition, the method may include positioning an instrument within the working lumen and proximate to the target area. The instrument may include an end effector for acting as an electrode. The method may further include emitting radiofrequency energy from the end effector and toward the target area. The method may also include receiving radiofrequency energy with the return electrode. The return electrode may include a clip that may be positioned outside the shaft of the medical device, and the method may also include coupling the clip to a surface of the target area.

The foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal."

BRIEF DESCRIPTION OF THE DRAWINGS

The accompanying drawings are incorporated in and constitute a part of this specification. These drawings illustrate aspects of the present disclosure that, together with the written descriptions herein, serve to explain this disclosure as follows:

FIGS. 2A and 2B illustrate perspective views of an electrosurgical device assembly according to aspects of the present disclosure.

DETAILED DESCRIPTION

Reference will now be made in detail to embodiments of the present disclosure, examples of which are illustrated in the accompanying drawings. Wherever possible, the same reference numbers will be used throughout the drawings to refer to the same or like parts. The term "distal" refers to the end farthest away from a user when introducing a device into a patient. The term "proximal" refers to the end closest to the user when placing the device into the patient. When used herein, the terms "approximately" and "substantially" may indicate a range of values within +/−5% of a stated value.

Exemplary embodiments of the present disclosure relate to systems, medical devices/surgical instruments, and methods for providing energy treatment to body tissue. In general, embodiments of the medical devices may include an electrically conductive end effector (e.g. conducts radio frequency energy) at a distal end of the device for contacting tissue within a patient's body. The electrically conductive end effector may act as an electrode to deliver therapeutic energy to portions of the body, such as tissue. The medical devices may also include a return electrode, an energy generator, a controller, and a user interface. The medical devices, or portions of the medical devices, may be inserted into a body lumen of a patient for intraluminal treatment, endoluminal procedures, laparoscopic procedures, and other medical procedures. The return electrode may be deployable or releasable within a body lumen of a patient and may contact tissue of the patient proximate to or at the site of treatment. The energy generator may input radio frequency energy waves into the end effector, and the radio frequency energy waves may be emitted out of the end effector, e.g. out of a distal tip of the end effector. The end effector may be used to cut, coagulate, desiccate, or fulgurate tissue within the body lumen of the patient. In some examples, the electrosurgical devices and assemblies may be used for treatment of endoscopic submucosal dissection (ESD).

Figure 1:
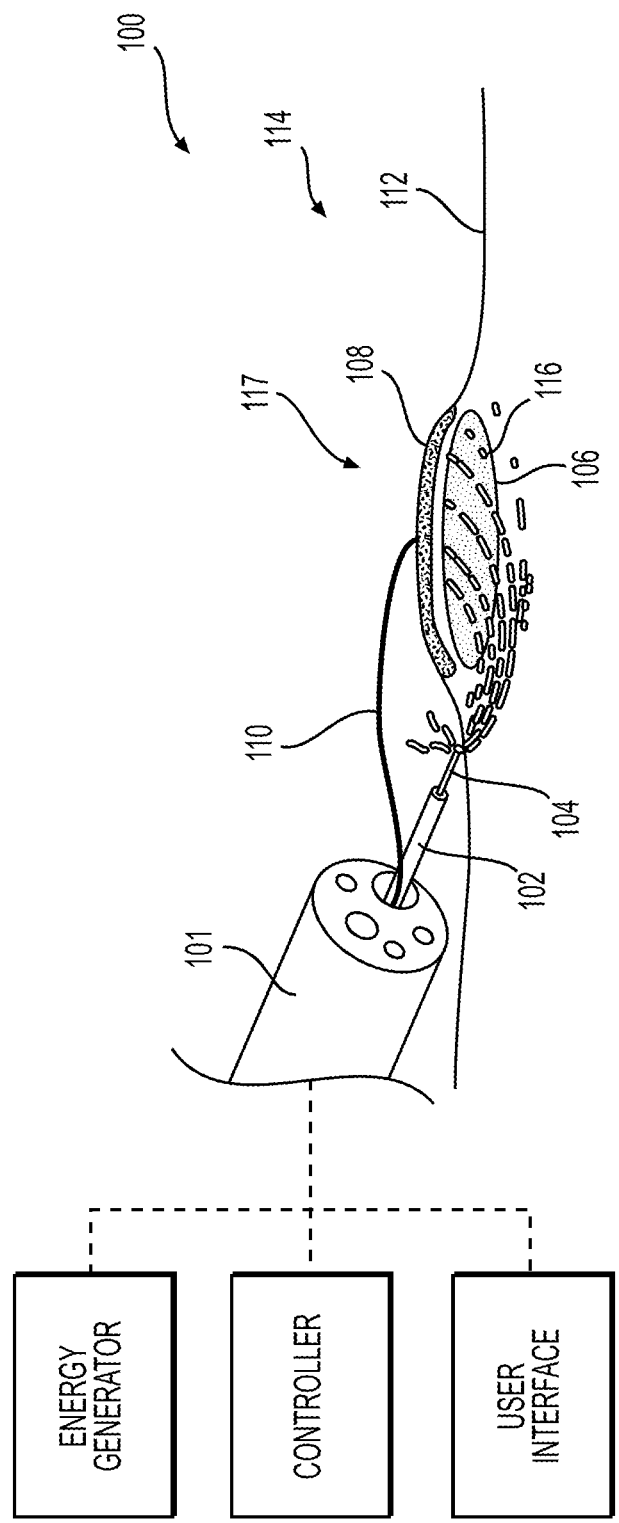
FIG. 1 illustrates a perspective view of an electrosurgical device assembly according to aspects of the present disclosure.

FIG. 1 illustrates an exemplary system 100 including a medical device 101 for providing energy treatment to tissue, in accordance with various embodiments of the present disclosure. As shown, the distal tip of medical device 101 may extend from a proximal end located outside a patient's body towards a distal end located within the body. The proximal end of the medical device 101 may include a handle configured to be held by a user of the medical device 101 and one or more actuators configured to be manipulated by the user to actuate portions of the medical device 101. The one or more actuators and/or handle may be used to steer, expand, collapse, actuate, etc., one or more portions of the medical device 101. In some examples, one or more lumens may extend in the proximal-distal direction along the length of the medical device 101. The proximal portion of medical device 101 may be connected to one or more devices external to the body of the patient, such as an energy generator 118, a controller 120, and a user interface 122. In some examples, medical device 101 may be an endoscope, gastroscope, colonoscope, delivery catheter, or other device for delivering a medical tool to a treatment site. The medical device 101 may further include one or more fluid lumens for delivery of various fluids, imaging lumens for components of one or more image sensors, vacuum lumens for suctioning air, liquid, or other material from near the distal tip of the medical device 101, and/or working lumens 105 for inserting one or more tools at the proximal end for use at the distal tip of the medical device 101. For example, a working lumen 105 of medical device 101 may be configured to receive an instrument 102 having an end effector 104 and/or a return electrode 108 for administering energy to portions of a patient's body, such as within a body lumen of the patient.

FIG. 1 illustrates a cross-section of a portion of a body lumen 114 including the lumen surface 112, a treatment site 117, and a lesion 106 where medical system 100 is administering energy 116 within the tissue defining body lumen 114. While exemplary embodiments of medical system 100 are shown administering energy 116 at treatment site 117 within a body lumen 114 of the patient, other examples of medical systems of the present disclosure may administer energy at treatment sites on the outer surface of the skin of a patient, or any other area of a patient's body.

Instrument 102 having end effector 104 may be inserted through a lumen of medical device 101, such as through working lumen 105, and extend from a surface at the distal tip of medical device 101. End effector 104 is configured to emit energy 116, such as radio frequency energy. In some examples, instrument 102 may not be inserted through a lumen of medical device 101, and instead may be inserted through a body lumen 114 of a patient and used at the treatment site separate from medical device 101. Return electrode 108 may be inserted in a lumen of medical device 101 and may be deployed at or proximate to the treatment site 117 to connect to a surface of the patient's tissue, such as surface 112 of body lumen 114. As shown in FIG. 1, energy 116 may flow from end effector 104 through a portion of the patient's body to return electrode 108.

Instrument 102 may have a conductive member extending along its longitudinal axis and coupled to end effector 104. End effector 104 may be needle shaped and/or may have a ball tip. At least a portion of the conductive member and end effector 104 of instrument 102 may be electrically insulated. End effector 104 may be used as an electrode for use in delivery of energy to tissue and may deliver energy 116 from the energy generator 118 to the treatment site 117. The conductive member and at least a portion of end effector 104 may be stainless steel, a tungsten alloy, NiTi, copper, an aluminum-based material, titanium, or any other conductive material. The conductive material may be insulated, and the insulation may be an encapsulation, jacket, sleeve, or stand offs providing an air gap to a sleeve. A stand off may include any suitable structure configured to insulate an inner sheath (e.g., around a wire) from an outer sheath. A stand off may be used, for example, when inner and outer sheaths are both conductive elements, to prevent them from touching by isolating them at periodic locations along their lengths with a nonconductive member. Examples of the nonconductive member could be an o-ring or any suitable protrusion (e.g., one or more dots) extending from the inner conductive element toward the outer conductive element, thereby keeping the conductive elements electrically-isolated from each other. In some examples, insulation may be a non-conductive thermoplastic, fluoropolymer, or elastomer such as polytetrafluoroethylene (PTFE), fluorinated ethylene propylene (FEP), silicone, perfluoroalkoxy polymer resin (PFA), or any other non-conductive material. The proximal end of instrument 102 may be connected to an energy source, such as a radio frequency energy source or an energy generator 118. Instrument 102 may be configured to connect to a monopolar mode of radiofrequency energy or a bipolar mode of radiofrequency energy, which will be further discussed later in this application. Instrument 102 may be extendable and/or retractable, and may be controlled using a handle of medical device 101, controller 120, user interface 122, or any other means. Energy 116 may be emitted from end effector 104, and the amount of energy 116 released from end effector 104 may be controlled using energy generator 118, controller 120, user interface 122, a handle of medical device 101, one or more actuators present on medical device 101, or a handle of instrument 102. End effector 104 may include a performing electrode, which may be a monopolar, bipolar or other type of electrode. Instrument 102 may be limited to receive an energy input source, for example may be limited to receive energy from energy generator 118. Energy 116 may be transferred to instrument 102 from energy generator 118 and may be radiofrequency energy.

Return electrode 108 may be configured to couple to a surface of tissue of a patient. In some examples, return electrode 108 may be configured to be releasably fixed to tissue of a patient, and may be adapted to be fixed to intraluminal tissue sites within the body of a patient. Return electrode 108 may include a fixation means, such as clips, barbs, adhesive, loops, sutures, micro-texture materials, quills, screws, spirals, radial reinforcement members, tacks or vacuum assisted fixation. Any of the fixation means used to couple return electrode 108 to a tissue surface of a patient may be absorbable and/or degradable. As shown in FIG. 1, return electrode 108 may have a substantially planar shape, and may have a wire or other conductive member 110 extending from the return electrode 108 to the energy generator 118. Return electrode 108 may be rectangular, circular, toroidal, or any other shape. Return electrode 108 may be flexible or rigid, and in some examples may be rolled and/or compressed to facilitate deployment within a body lumen of a patient. In some examples, return electrode 108 may have a retracted state and an expanded state. A surface of the return electrode 118 may have a traction mechanism, such as perforations, spikes, or irregularities to assist in fixing return electrode 108 to a surface of tissue. In some examples, conductive member 110 may be coupled to return electrode 108 via a clip, a fastener, alligator clip, and/or may be pressed against return electrode 108 by a surgical tool. In some examples, multiple conductive members 110 may be used and coupled to one or more return electrodes 108. For example, two return electrodes 108 and two conductive members 110 may be used, with one conductive member 110 connected to one return electrode 108 and the other conductive member 110 connected to the other return electrode 108. In some examples, multiple return electrodes 108 and conductive members 110 may serve as the return path for radiofrequency energy.

In some examples, return electrode 108 may be a wire or other fixed object that may be inserted into a body lumen of a patient and applied to the surface of the tissue without fixing the return electrode 108 to the surface of the tissue. In some examples, return electrode 108 may be deployed through an endoscope's working channel, such as working channel 105, alongside an endoscope, or be delivered to the treatment site 117 via a stand-alone delivery tube (not shown). In some examples, the return electrode of any of the medical systems described herein may act as the end effector and deliver energy to tissue of the patient and the instrument including an end effector may act as the return electrode. In some examples, multiple return electrodes 108 may be used and deployed, and may be the same or different material.

The energy generator 118 may supply any suitable energy, such as electrical, laser, thermal, ultrasound, etc. In some examples, energy generator 118 may generate radiofrequency energy. The controller 120 and the user interface 122 may include various components, such as processors for processing instructions (e.g. program instructions), memory, and user input devices. The controller 120 and the user interface 122 may modulate the characteristics of the energy supplied to the medical system 100. The user interface 122 may display the energy output of instrument 102 and/or may display an image of the treatment area 117, such as an image from an imaging sensor present at the distal tip of medical device 101. One or more actuation mechanisms, such as buttons, dials, sensors, etc., may be present on the energy generator 118, the controller, 120, and/or the user interface 122. In some examples, the deployment and/or release of return electrode 108 may be controlled via an actuator on energy generator 118, the controller 120, and/or the user interface 122. In some examples, the user may adjust the energy output of instrument 102 via one or more actuators on the energy generator 118, the controller 120, and/or the user interface 122.

In some examples, the energy generator 118 may output, and the medical system 100 and/or medical device 101 may be configured for, 70 Watts peak power in a bipolar mode and 95 Watts peak power in a monopolar mode. In other examples, the energy generator 118 may output, and/or the medical system 100 and/or medical device 101 may be configured for, 70, 50-100, 120, 170, 170-430, 250, 300-370, or 390-770 Watts peak power in a bipolar mode and 300, 200-300, 570-650, 770-1710, or 740-1450 Watts peak power in a monopolar mode. Any of these ranges of peak power, along with any other range of peak power not otherwise specified, may be used in any of the disclosed medical systems described herein.

FIGS. 2A and 2B illustrate an exemplary embodiment of a medical system 200 including medical device 201, an instrument 202 with end effector 204, a return electrode 208 and conductive member 210 connected to return electrode 208, all of which may have any of the previously described features in relation to medical system 100. In FIG. 2A, return electrode 208 is deployed in a retracted configuration from a working lumen 205 of medical device 201. In some examples, return electrode 208 may be deployed using an air or water jet, a tension release mechanism such as loosening of conductive member 210, or may be pushed out of the working lumen 205 by a tool such as the instrument 202. When deployed and/or after exiting the working lumen 205 of medical device 201, return electrode 208 may transition from a retracted state (shown in FIG. 2A) to an expanded state (shown in FIG. 2B). In some examples, return electrode 208 may expand when deployed similar to a parachute and may adhere to the surface 212 of the treatment site 217 via an adhesive or other attachment mechanism present on a surface of return electrode 208.

In other examples, return electrode 208 may transition from a retracted state to an expanded state with the assistance of a spring mechanism triggered when exiting the working lumen 205 of medical device 201. In other examples, return electrode 208 may include one or more of the attachment and/or expansion mechanisms disclosed herein. In another example, return electrode 208 may include shape-memory material, such as Nitinol, so that it attains an expanded shape upon exit from lumen 205. Return electrode 208 may be coupled to surface 212 on a lesion 216 within the treatment area 217, to surface 212 proximate to a lesion 216, or proximate to treatment site 217 which may or may not contain a lesion 216. Return electrode 208 may be deployed proximate to a target area, such as treatment area 217, within the body of patient, and when return electrode 208 is positioned proximate to a target area, return electrode 208 may be coplanar with the target area, may be adjacent to the target area, may be intraluminal within the patient's body, or attached to the target area. After return electrode 208 is deployed and coupled to tissue surface 216 of the treatment site 217, instrument 202 may be deployed and energy from the energy generator 118 may be administered to the treatment site 217 from end effector 204. Return electrode 208 may provide a mechanism for the energy emitted from end effector 204 to travel back to the energy generator 118, preventing energy from traveling through other parts of the body of the patient. The local deployment of return electrode 208 may enable instrument 202 to utilize a lower overall energy level from energy generator 118, which may enable the user to use a smaller instrument and end effector to conduct a procedure. In some examples, a procedure ordinarily performed using an energy level associated with monopolar electrosurgery may be performed using medical system 200 with an energy level associated with bipolar electrosurgery. In some examples, the energy density (Joules/area) or power density (Watts/area) and the temporal change of the energy/power density may be decreased by using medical systems disclosed herein compared to electrosurgical procedures known in the art.

Figure 3:
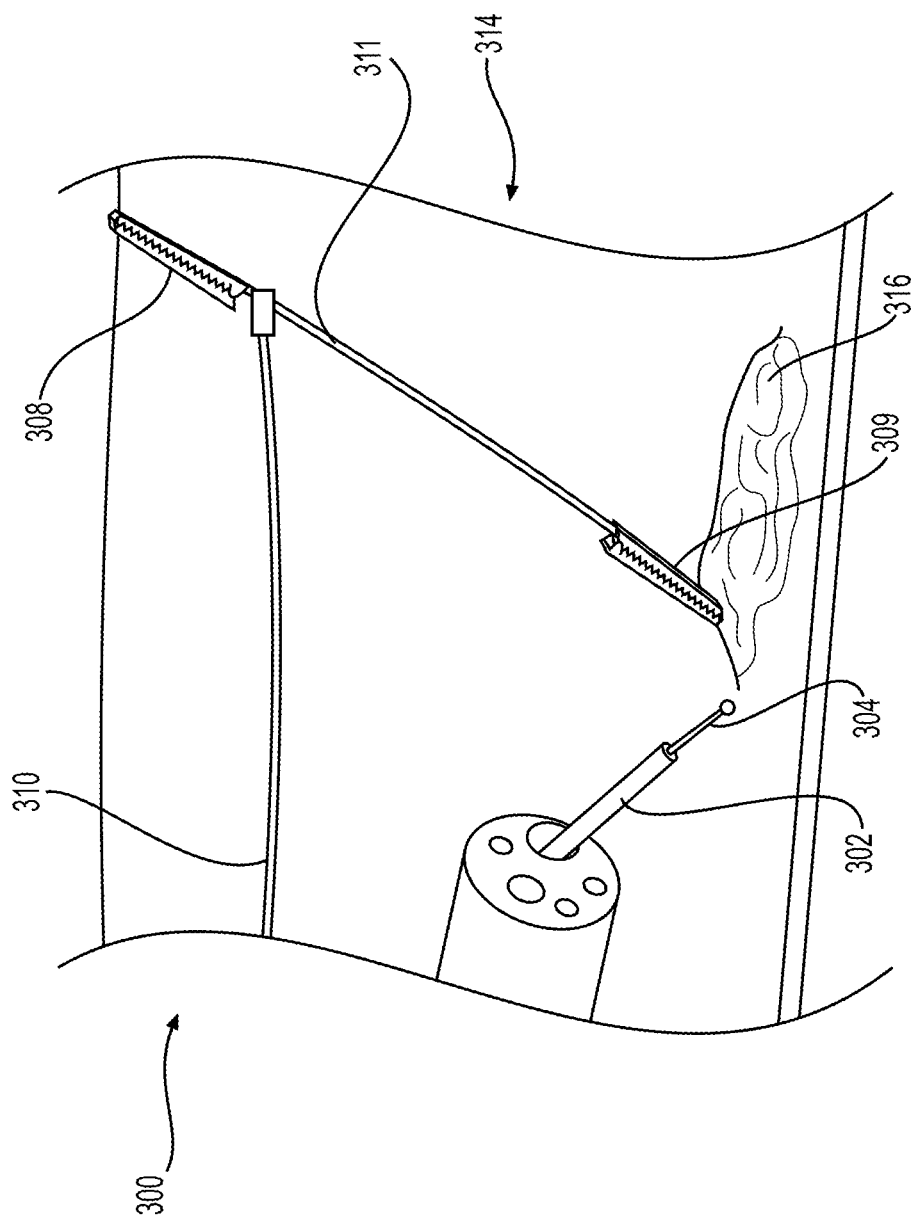
FIG. 3 illustrates a perspective view of an electrosurgical device assembly according to aspects of the present disclosure.

FIG. 3 illustrates a perspective view of a cross-section of a body lumen 314 of a patient. FIG. 3 shows another exemplary embodiment of a medical system 300 similar to previously described medical systems 100, 200. Medical system 300 includes medical device 301, instrument 302 including end effector 304, return electrode 311 including clips 308, 309, clip connector 318 and wire 310. Any of the components of medical system 300 may have any of the characteristics described herein in relation to the other medical systems. As shown in FIG. 3, return electrode 311 may include multiple clips 308, 309 that may be coupled to surface 312 of body lumen 314 and may provide a means of tensioning surface 312, lesion 316, and/or treatment site 317. Clips 308, 309 of return electrode 311 may be connected via clip connector 318 (e.g. a wire) or other means, may create an adirectional force applied to body lumen 314, and may create tension on surface 312, at treatment site 317, and/or at lesion 316. Return electrode 311 including clips 308, 309 may be deployed using forceps or any other means of fastening clips 308, 309 to surface 312 of body lumen 314. Tension created by an adirectional force from clips 308, 309 may assist with cutting surface 312 or lesion 316 with energy emitted from end effector 304. Energy emitted from end effector 304 may travel through clips 308, 309 and clip connector 318 of return electrode 311, and through wire 310 back to energy generator 118.

Figure 4:
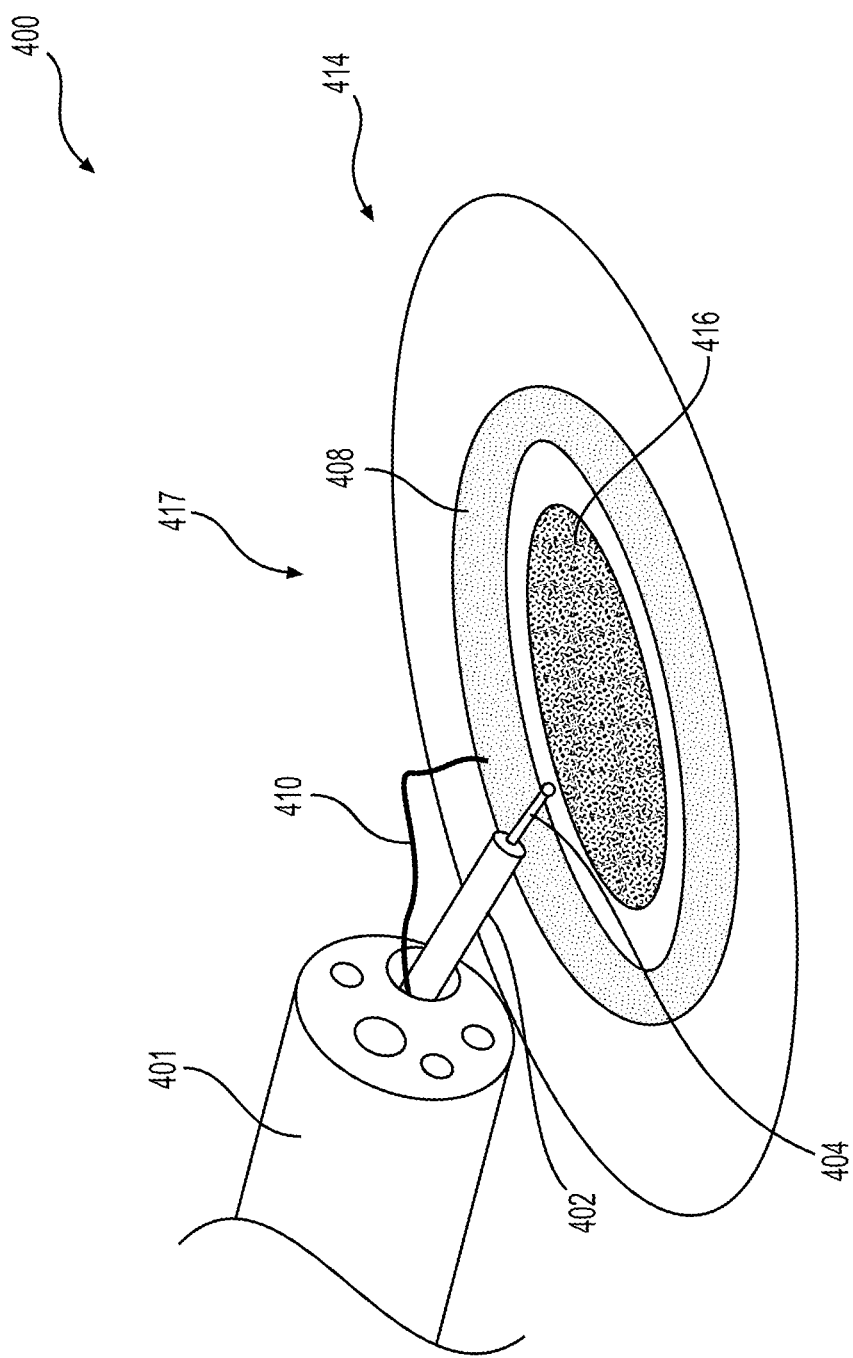
FIG. 4 illustrates a perspective view of an electrosurgical device assembly according to aspects of the present disclosure.

FIG. 4 illustrates another exemplary embodiment of medical system 400 including medical device 401, instrument 402 with end effector 404, return electrode 408 and connecting member 410. Medical system 400 may be substantially the same as medical systems 100, 200, and 300, and may have any of the characteristics of components and use any deployment methods described herein in relation to other medical systems. In some examples, return electrode 408 may have a toroidal and/or ring shape, and may be positioned around lesion 416 within treatment site 417 and/or body lumen 414. While FIG. 4 shows a ring-shaped return electrode 408 surrounding lesion 416, return electrode 408 may have any other shape that may partially or completely surround lesion 416 at treatment site 417.

Figure 5:
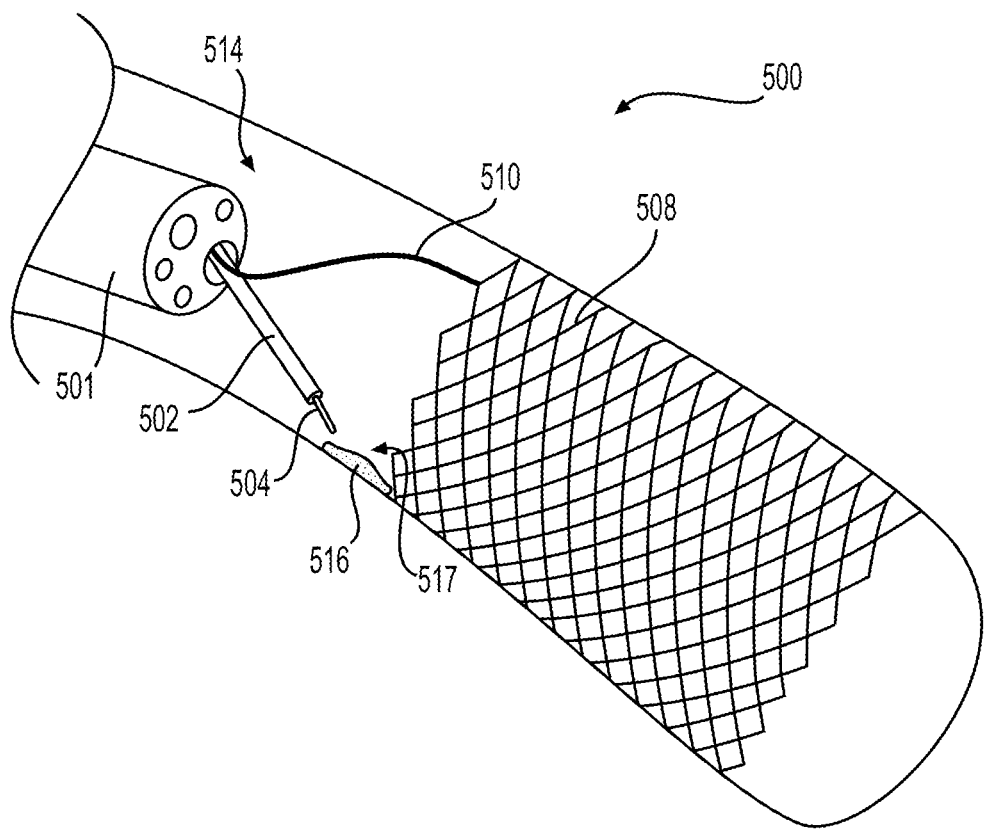
FIG. 5 illustrates a perspective view of an electrosurgical device assembly according to aspects of the present disclosure.

FIG. 5 illustrates yet another exemplary embodiment of medical system 500 including medical device 501, instrument 502 including end effector 504, return electrode 508, connecting member 510, all of which may have any of the characteristics described herein in relation to other medical systems. In FIG. 5, a cross-sectional perspective view of a body lumen is shown with return electrode 508 coupled to body lumen 514 and end effector 504 at treatment site 517. In some examples, return electrode 508 may be a stent, such as an AXIOS™ stent. Return electrode 508 may create tension around the inner radial surface of the body lumen 514: Return electrode 508 may expand when released from a working channel of medical device 501 and/or when deployed by the user. By utilizing return electrode 508, the body lumen 514 of a patient may be expanded and may increase the visibility and/or working space to conduct an electrosurgical procedure.

Figure 6:
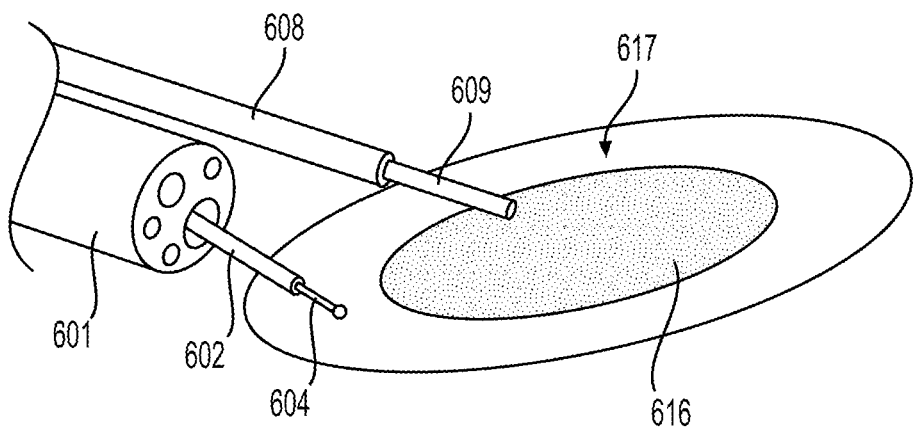
FIG. 6 illustrates a perspective view of an electrosurgical device assembly according to aspects of the present disclosure.

FIG. 6 illustrates another exemplary medical system 600 similar to the previously described medical systems and including medical device 601, instrument 602 with end effector 604, and return electrode 609. However, return electrode 609 is positioned using a separate tool 608 instead of via medical device 601. Electrode 609 may be connected to energy generator 118 and may be exposed at the distal end of tool 608. The return electrode 609 may be positioned to contact a surface of treatment site 617, such as touching lesion 616, to allow energy to travel from end effector 604, through parts of the treatment site 617 to return electrode 609 and back to energy generator 118. By utilizing tool 608 to deliver return electrode 609 to the treatment site 617, more space may be available within medical device 601 for other purposes, such as inserting additional tools through any working lumens within medical device 601.

Figure 7:
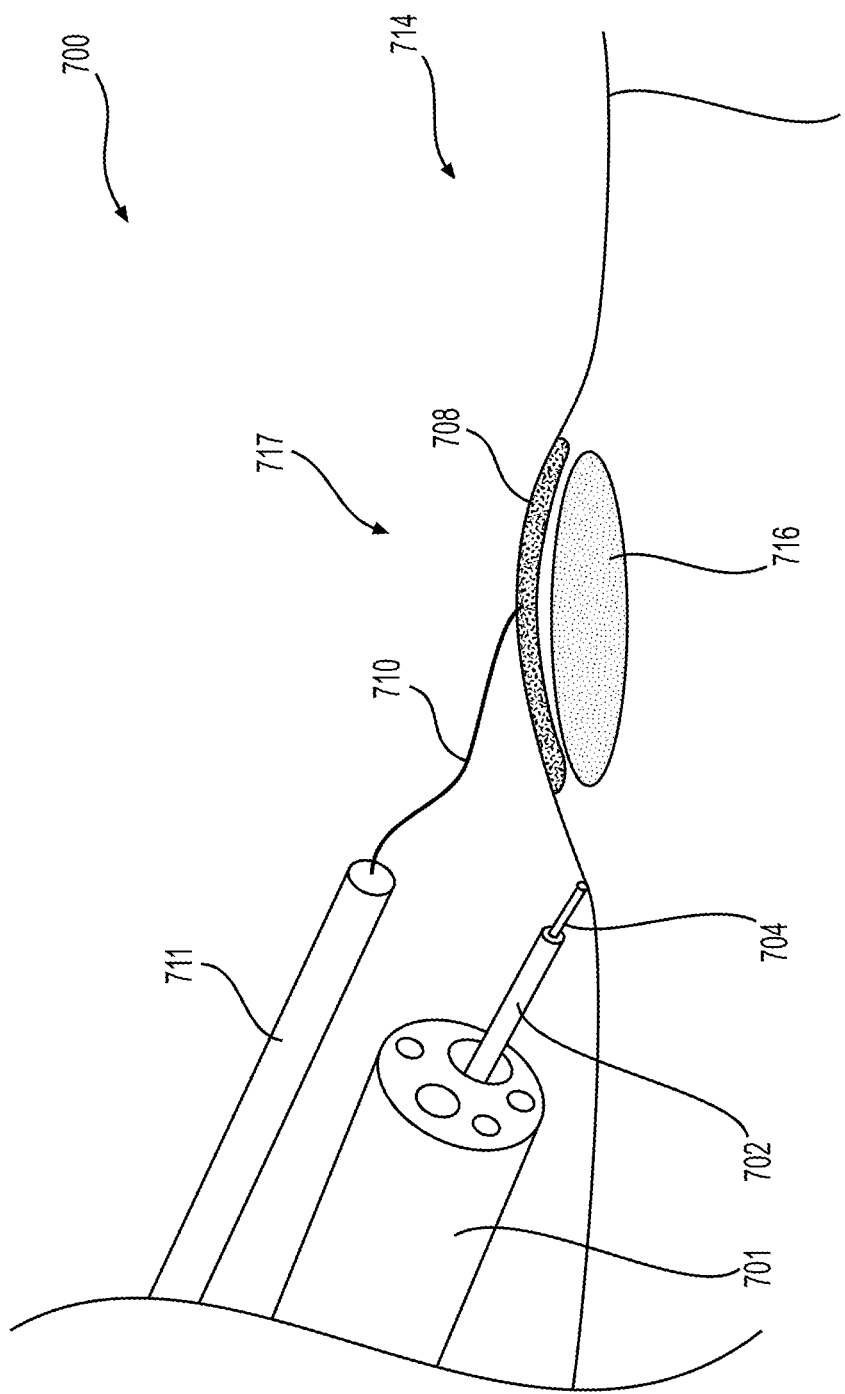
FIG. 7 illustrates a perspective view of an electrosurgical device assembly according to aspects of the present disclosure.

FIG. 7 illustrates an exemplary medical system 700 substantially similar to medical system 600, including medical device 701, instrument 702 including end effector 704, return electrode 708, connecting member 710, and tool 711. Medical system 700 may have any of the characteristics of other medical systems described herein. Return electrode 708 may be connected to connecting member 710 (e.g. a wire), which extends through tool 711. Tool 711 provides a means to deploy return electrode 708 separate from medical device 701, and may assist in positioning return electrode 708 on surface 712 of body lumen 714 and/or proximate to lesion 716. Return electrode 708 may be positioned on surface 712 by any means described herein in relation to other medical systems, and may be deployed or released from tool 711. Conductive member 710 and electrode 708 may be connected to energy generator 118 to allow energy emitted from end effector 704 to travel through portions of treatment site 717 and back to energy generator 118.

Figure 8:
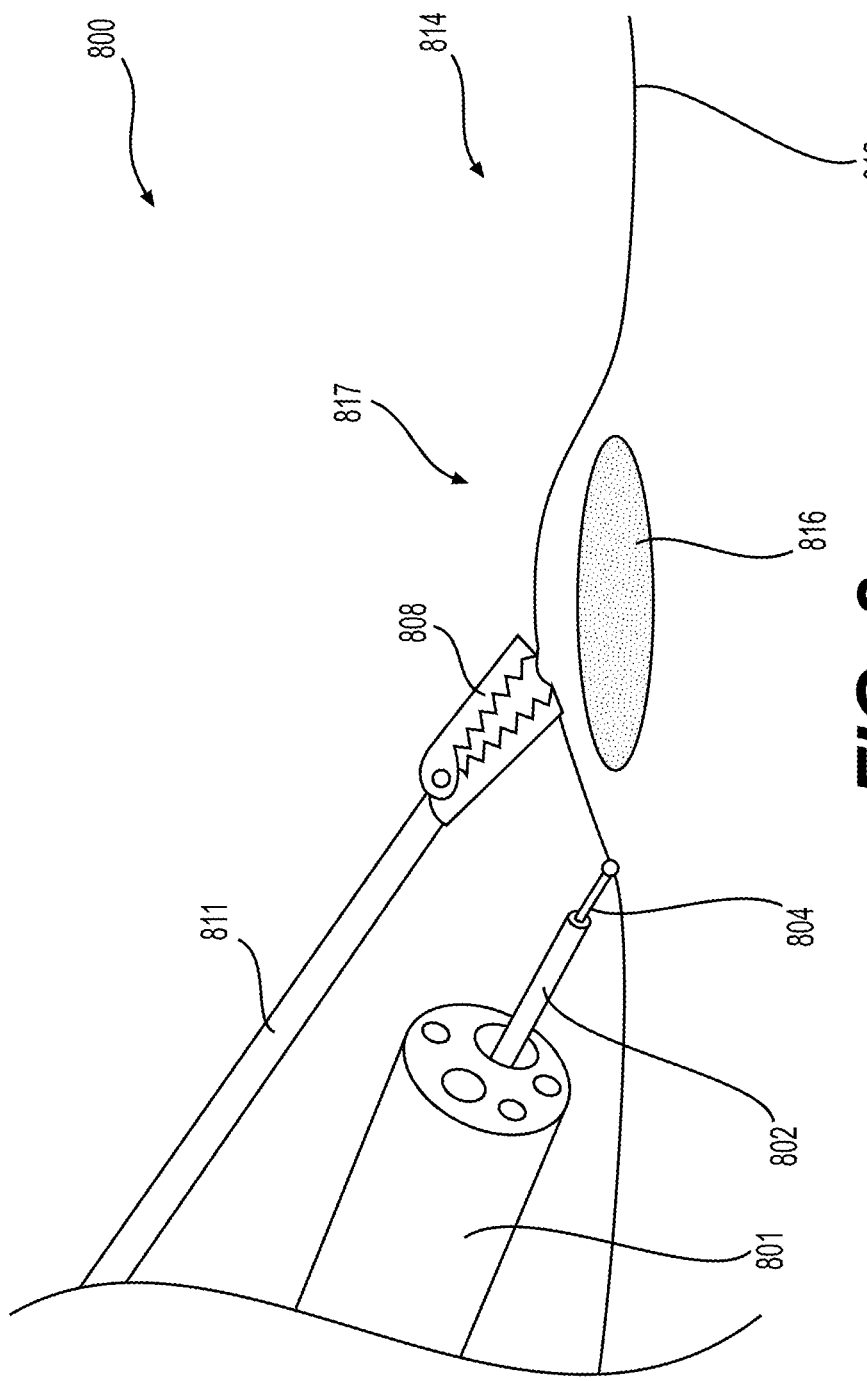
FIG. 8 illustrates a perspective view of an electrosurgical device assembly according to aspects of the present disclosure.

FIG. 8 illustrates another exemplary medical system 800 similar to the previously described medical systems and including medical device 801, instrument 802 with end effector 804, and return electrode 808. Medical system 800 is substantially similar to medical system 700, except tool 811 includes a clip 808 that acts as a return electrode. Tool 811 and its clip 808 may be separate from medical device 801 and may be coupled to surface 812 to assist with tensioning surface 812 and/or lesion 816 during a procedure. Tool 811 may be configured to be positioned within body lumen 814 and clip 808 may be configured to couple to a treatment site 817 within body lumen 814.

Figure 9:
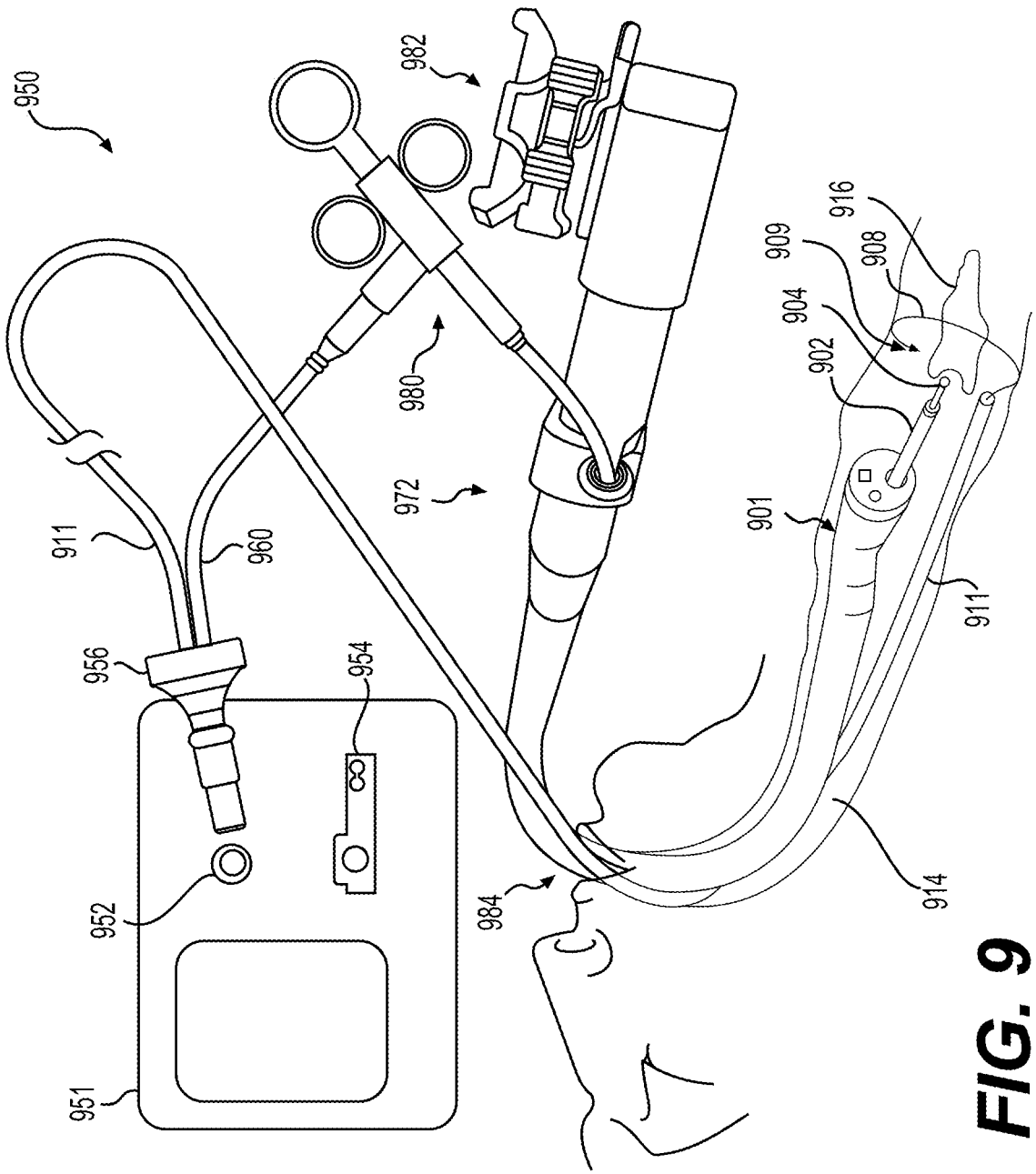
FIG. 9 illustrates a medical system according to an aspect of the disclosure.

FIG. 9 illustrates another exemplary medical system 950 similar to the previously described medical systems. FIG. 9 illustrates a perspective view of a cross-section of a body lumen 914 of a patient and exemplary medical system including medical device 901, instrument 902 with end effector 904, tool 911, and return electrode 908 with a hook 909 at the distal tip of return electrode 908. Medical device 901 may be inserted through an opening 984 (such as a mouth) of a body lumen 914 to reach a target lesion 916 for treatment. Return electrode 908 may be a wire extending in a proximal-distal direction, may extend outward from a distal tip of tool 911, and may be electrically insulated. Return electrode 908 may include a curved distal portion with a hook 909 at its distal tip to assist with coupling return electrode 908 to a surface of body lumen 914 proximate to target lesion 916. In some examples, return electrode 908 may surround lesion 916 partially or completely.

FIG. 9 also shows the proximal portion of medical system 950 outside the body of the patient. In some examples, the proximal portion of medical system 950 may include proximal portion 972 of medical device 901, which may have a handle and control knobs 982 for articulation and locking of the distal end of device 901. In some examples, instrument 902 and tool 911 may both be connected to energy generator 951 through a single connector 956. Connector 956 may be releasably connected to energy generator 951. In other examples, connector 956 may be permanently coupled to energy generator 951. In some examples, energy generator 951 may include a bipolar receptacle 952 and a monopolar receptacle 954, and connector 956 may be connected to energy generator 951 through bipolar receptacle 952. In other examples, connector 956 may be connected to energy generator 951 through monopolar receptacle 954. Connector 956 therefore provides current from generator 951 to tool 911 and through a connecting portion 960 to end effector 904. In some examples, connecting portion 960 may connect connector 956 to an actuator 980, which is connected to instrument 902. In some examples, the proximal portion of tool 911 and/or connecting portion 960 and/or instrument 902 may include a user interface for actuation of end effector 904. In some examples, actuator 980 and/or a user interface of tool 911 and/or connecting portion 960 and/or instrument 902 may control one or more components of medical system 950 and may open, close, extend, retract, cut, coagulate, articulate, and/or apply a fluid jet of one or more components of medical system 950. Any of the medical systems discussed herein may utilize a similar connector as connector 956 and may include a similar proximal portion of the medical system as the proximal portion of medical system 950.

Any of the medical systems disclosed herein may operate in a monopolar mode or a bipolar mode. In particular, energy generator 118 may be in a monopolar mode or bipolar mode. In some examples, bipolar mode may use lower voltages while monopolar mode may require higher voltages. Since the medical device assemblies of the present disclosure include return electrodes positioned at the site of treatment within the body of the patient, the power density away from the treatment site is lower than conventional monopolar electrosurgery, where the return electrode is positioned somewhere on the patient's exterior skin, typically not proximate to the site of surgery. By positioning the return electrode proximate to the site of surgery within the body, medical device assemblies of the present disclosure may have similar efficiency and effectiveness as conventional monopolar electrosurgical techniques while outputting significantly lower energy levels and with a much lower risk of unwanted thermal perforation.

Each of the aforementioned medical device assemblies, whether used with an endoscope, tool, or any other medical device, may be used to treat and/or remove a patient's tissue. In some examples, the user may locate a treatment site (such as a tumor, lesion, or other diseased tissue) present in a body lumen of a subject using an endoscope or other tool by directly visualizing the treatment site using an image sensor. The image sensor may show the user the surface of a treatment site, such as treatment site 117 in FIG. 1. Any of the aforementioned medical devices or components of medical device assemblies may be used to deploy a return electrode at or proximate to the treatment site. For example, return electrode 108 may be deployed from medical device 101 and may couple to surface 112 of treatment site 117. Subsequently, an end effector, such as end effector 104, may be positioned proximate to the treatment site. Once the user has initiated energy emission, such as actuating an actuator on medical device 101, instrument 102, user interface 122, or controller 120 to emit energy from the end effector 104, an energy generator may transmit radiofrequency energy to the instrument to be emitted from the end effector 104 to treat the treatment site or a portion thereof. The return electrode then may receive radiofrequency energy waves from the treatment site, and the radiofrequency energy waves may travel through the return electrode back to energy generator or to a ground source. Additionally, the end effector may ablate, dissect, coagulate, fulgurate and/or cut target tissue using radiofrequency energy. In some examples, the return electrode may dissolve or release from the surface of the patient's tissue after completing the surgery.

By using one or more of the medical devices described herein on the distal end of an endoscope, in conjunction with an endoscope, and/or on the distal end of a tool, users can administer radiofrequency energy to a treatment site within the body of a patient and reduce the risks associates with ordinary monopolar electrosurgery.

It should be understood that one or more of the aspects of any of the medical devices and medical device assemblies described herein may be used in combination with any other medical device or medical device assembly known in the art, such as medical imaging systems, tools such as forceps, water jets, or vacuum systems, or combined with known embodiments of endoscopes.

It also should also be understood that one or more aspects of any of the medical devices described herein may be used for cutting, dissecting, treating, or ablating tissue in any part of the human body. For example any of the medical devices described herein may be used in medical procedures such as for Endoscopic Submucosal Dissection (ESD), cancer treatment, and/or other procedures where removal, dissection, fulguration and/or ablation of the type of tissue is needed.

Although the exemplary embodiments described above have been disclosed in connection with medical devices for providing electric energy treatment of human tissue through the working channel of a medical device, a natural orifice, or by incision, a person skilled in the art will understand that the principles set out above can be applied to any electrosurgery device and can be implemented in different ways without departing from the scope of the disclosure as defined by the claims. In particular, constructional details, including manufacturing techniques and materials, are well within the understanding of those of skill in the art and have not been set out in any detail here. These and other modifications and variations are well within the scope of the present disclosure and can be envisioned and implemented by those of skill in the art.

Moreover, while specific exemplary embodiments may have been illustrated and described collectively herein, it should be appreciated that any subsequent arrangement designed to achieve the same or similar purpose may be substituted for the specific embodiments described and shown herein. This disclosure is intended to cover any and all subsequent adaptations or variations of various embodiments. Combinations of the above embodiments, and other embodiments not specifically described herein, will be apparent to those of skill in the art upon reviewing the description.

Other exemplary embodiments of the present disclosure will be apparent to those skilled in the art from consideration of the specification and practice of the exemplary embodiments disclosed herein. It is intended that the specification and examples be considered as exemplary only, and departures in form and detail may be made without departing from the scope and spirit of the present disclosure as defined by the following claims.

We claim:

1. A medical system comprising:
an instrument including a performing electrode at a distal end of the instrument, wherein the distal end of the instrument is configured to be positioned in a body of a subject and the performing electrode is configured to emit radiofrequency energy towards a target area in the body; and
a return electrode deliverable within the body proximate the target area, separately from the instrument and external to the instrument, wherein the return electrode is configured to be separately movable relative to the instrument, contact tissue in the body proximate the target area, and receive radiofrequency energy emitted from the performing electrode, wherein the return electrode includes a central lumen configured to receive the target area.

2. The medical system of claim 1, further comprising an energy source for delivering radiofrequency energy to the performing electrode and receiving radiofrequency energy from the return electrode.

3. The medical system of claim 2, further comprising a conductive member configured to be coupled to the return electrode, and extend proximally from the return electrode to the energy source.

4. The medical system of claim 3, wherein the conductive member is configured to extend proximally from a second side of the return electrode opposite a first side of the return electrode that is configured to contact the tissue.

5. The medical system of claim 1, wherein the return electrode includes one or more fixation mechanisms configured to releasably fix the return electrode to a surface of the tissue.

6. The medical system of claim 1, further comprising a shaft having a distal end and a plurality of lumens, wherein:
the instrument is deliverable in a first lumen of the plurality of lumens; and
the return electrode is deliverable in the first lumen, a second lumen of the plurality of lumens, external of the shaft, or via a delivery device separate from the shaft.

7. The medical system of claim 1, wherein the return electrode has an expanded state and a retracted state.

8. The medical system of claim 7, wherein the return electrode is configured to transition from the retracted state to the expanded state when deployed from a lumen of a delivery device.

9. The medical system of claim 8, wherein one or more of a spring mechanism, a tension release mechanism, a tool, an air jet, or a water jet is used to deploy the return electrode from the lumen.

10. The medical system of claim 7, wherein the return electrode is flexible and has a substantially planar shape in the expanded state.

11. The medical system of claim 1, further comprising a tool including the return electrode at a distal end of the tool, wherein the tool is deliverable, separately from and separately movable relative to the instrument.

12. A medical system comprising:
   an instrument including a performing electrode at a distal end of the instrument, wherein the distal end of the instrument is configured to be positioned in a body lumen of a subject and the performing electrode is configured to emit radiofrequency energy towards a treatment site located on a first portion of an inner radial surface the body lumen; and
   a return electrode deliverable within the body lumen proximate the treatment site, separately from the instrument and external to the instrument, wherein the return electrode is configured to be separately movable relative to the instrument and at least partially contact a plurality of portions of the inner radial surface of the body lumen including the first portion, and receive radiofrequency energy emitted from the performing electrode.

13. The medical system of claim 12, wherein the return electrode includes a first clip configured to contact the first portion, a second clip configured to contact a second portion of the inner radial surface of the body lumen different from the first portion, and a connector connecting the first clip and the second clip.

14. The medical system of claim 13, further comprising a conductive member coupled to the connector.

15. The medical system of claim 12, further comprising a shaft having a distal end and a plurality of lumens, wherein the instrument is deliverable in a first lumen of the plurality of lumens; and
   wherein the return electrode is deliverable through a delivery device that is separate from the shaft.

16. The medical system of claim 13, wherein the first clip and the second clip are configured to create tension at the treatment site, and wherein the tension applies a force that moves the first clip and the second clip in a direction away from the instrument.

17. A medical system comprising:
   an instrument including a performing electrode at a distal end of the instrument, wherein the distal end of the instrument is configured to be positioned in a body of a subject and the performing electrode is configured to emit radiofrequency energy towards a target area in the body; and
   a tool including a return electrode at a distal end of the tool, wherein the tool is deliverable, separately from the instrument, within the body proximate the target area, wherein the return electrode is configured to couple to at least a portion of the target area, and receive radiofrequency energy emitted from the performing electrode.

18. The medical system of claim 17, wherein the return electrode includes a clip at the distal end of the tool configured to couple to at least the portion of the target area.

19. The medical system of claim 17, wherein the return electrode includes a wire comprising a curved distal portion having a hook at a distal tip of the curved distal portion, the hook configured to couple the return electrode to at least the portion of the target area.

20. The medical system of claim 17, wherein the tool is separately movable relative to the instrument, and wherein the tool is configured to position the return electrode within the body proximate the target area.

* * * * *